United States Patent [19]

Petzoldt

[11] Patent Number: 5,275,936
[45] Date of Patent: Jan. 4, 1994

[54] PROCESS FOR THE PREPARATION OF 1-METHYL-1,4-ANDROSTADIENE-3,17-DIONE

[75] Inventor: Karl Petzoldt, Berlin, Fed. Rep. of Germany

[73] Assignee: Schering Aktiengesellschaft, Berlin and Bergkamen, Fed. Rep. of Germany

[21] Appl. No.: 863,666

[22] Filed: Apr. 6, 1992

Related U.S. Application Data

[63] Continuation of Ser. No. 647,961, Jan. 30, 1991, abandoned, which is a continuation of Ser. No. 14,040, Dec. 3, 1986, abandoned.

[30] Foreign Application Priority Data

Apr. 3, 1985 [DE] Fed. Rep. of Germany ....... 3512328

[51] Int. Cl.$^5$ ................ C12P 33/02; C12P 33/00; C12N 1/20
[52] U.S. Cl. ........................... 435/61; 435/52; 435/872; 435/863; 435/253.1; 435/253.2
[58] Field of Search ............... 435/61, 52, 132, 253.1, 435/253.2, 872, 863

[56] References Cited

U.S. PATENT DOCUMENTS 3,364,237 1/1968 Diassi et al. .
3,526,576 9/1970 Pan et al. .
4,591,585 5/1986 Kerb ..................................... 514/177

OTHER PUBLICATIONS

ATCC catalogue of Bacteria, 1992, pp. 271–272.
USAN and the USP Dictionary of Drug Names, 25th Ed. (current through Jun., 1987).
J. Am. Chem. Soc. 87, 1385 (1965).
J. Am. Chem. Soc. 87, 2765 (1965).
Bioch. Biophys. Acta 93, 398 (1964).
Biotech. Bioeng. XI, 1183 (1969).
Goodfellow et al. "Biology of the Actinomycets" 1984, Academic Press, p. 92.
ATCC Catalog of Bacteria, 1985, pp. 150–151.
Vischer et al. *Experientia*, vol. 9, pp. 317–372, 1953.
Nambara et al., *Chem Pharm. Bull*, vol. 21, 1973, pp. 2794–2796.
Tamaki et al., *J. of Biochem*, vol. 45, 1958 pp. 693–698.

*Primary Examiner*—Irene Marx
*Attorney, Agent, or Firm*—Millen, White, Zelano, & Branigan

[57] ABSTRACT

A process is claimed for the preparation of 1-methyl-1,4-androstadiene-3,17-dione characterized by fermenting 1-methyl-5α-androst-1-ene-3,17-dione (metenolone) with a microorganism culture of the genera Nocardia, Mycobacterium, or Fusarium.

4 Claims, No Drawings

PROCESS FOR THE PREPARATION OF 1-METHYL-1,4-ANDROSTADIENE-3,17-DIONE

This us a continuation of Ser. No. 07/647,961 of Jan. 30, 1991, which is a continuation of Ser. No. 07/014,040 of Dec. 3, 1986, now abandoned which is based on PCT/DE86/00130 of Mar. 26, 1986.

The invention comprises a process for the preparation of 1-methyl-1,4-androstadiene-3,17-dione, comprising fermenting 17$\beta$-hydroxy-1-methyl-5$\alpha$-androsten-1-en-3-one (methenolone) with a microorganism culture of the genera Nocardia, Mycobacterium or Fusarium. The invention also comprises a process for the preparation of 1-methyl-1,4-androstadiene-3,17-dione, comprising fermenting 17$\beta$-hydroxy-1-methyl-5$\alpha$-androsten-1-en-3-one with a microorganism culture of the species Nocardia corallina ATCC 14350, *Mycobacterium rhodochrous* ATCC 4276 (both now reclassified as strains of the species *Rhodococus rhodochrous*), or *Fusarium solani* ATCC 12823.

The process of this invention is performed under the conditions usually applied in microbiological dehydrogenation of substrates by means of microorganism cultures. Thus, first of all, in generally customary preliminary tests, the most favorable fermentation conditions are determined analytically, especially by thin-layer chromatography, such as the most advantageous fermentation conditions, for example choice of most beneficial nutrient medium, suitable substrate solvent or suspension agent, substrate concentration, the technical conditions, such as temperature, aeration, pH value, and optimum times for germination, addition of substrate, and substrate contact on the enzyme of the microorganism.

It has been found, in this connection, that it is advantageous to employ concentrations of about 100–2,000 mg of substrate per liter of nutrient medium. The pH is preferably set at a value ranging from 5 to 7. The incubation temperature ranges from 20° to 40° C., preferably 25°–35° C. For aeration, preferably 0.5–5 liters of air is introduced per minute per liter of culture broth. Conversion of the substrate is suitably monitored by analyses of sample extracts.

The microorganisms required for this fermentation are freely available to the professional community from recognized collections of microorganisms. Suitable strains are Nocardias, such as Nocardia corallina ATCC 14350, Mycobacteria, such as Mycobacterium rhodochrous ATCC 4276, or Fusaria, such as Fusarium solani ATCC 12823.

After fermentation has taken place, the fermentation products are conventionally isolated. Isolation can be conducted, for example, by extracting the fermentation batches in an organic solvent immiscible with water, such as ethyl acetate, butyl acetate, or methyl isobutyl ketone; concentrating the extracts; and purifying the thus-obtained crude products optionally by chromatography and/or crystallization.

The practical examples set forth below serve for explaining the process of this invention.

EXAMPLE 1

A 2-liter Erlenmeyer flask with 500 ml of a nutrient solution sterilized for 30 minutes at 120° C. in an autoclave, consisting of 0.5% dextrose monohydrate, 0.5% yeast extract, 0.2% corn steep liquor, and 0.1% peptone, pH 7.5, is inoculated with an agar slant of the strain *Nocardia corallina* ATCC 14350 and shaken for 48 hours on a rotary shaker at 30° C.

A 20-liter preliminary fermentor, charged with 15 l of a nutrient medium having the same composition as the incubating culture and having been sterilized for 30 minutes at 121° C. and under an excess pressure of 1.1 bar, is inoculated with 250 ml of this incubating culture. With addition of "silicone SH" as the antifrothing agent, germination is conducted at 29° C. and an excess pressure of 0.7 bar for 24 hours under aeration (15 l/min) and agitation (220 rpm).

Thereafter, 0.9 l of this preliminary fermentor culture is withdrawn under sterile conditions and used for inoculating a 20-liter main fermentor containing 14 l of sterilized nutrient solution of the same composition as the preliminary fermentor culture. After a growth phase of 6 hours under preliminary fermentor conditions, a sterile-filtered solution of 4.5 g of methenolone in 60 ml of dimethylformamide is added thereto and the batch is further stirred and aerated.

After a contact period of 56 hours, the reaction is finished. The culture broth is extracted with methyl isobutyl ketone, using one-half and thereafter twice respectively one-third of the culture volume; the extracts are combined and concentrated to dryness under vacuum. For removing the antifrothing agent, the residue is taken up in methanol, filtered off from the undissolved antifrothing agent through a double-folded filter, the solution is treated with activated carbon and again concentrated to dryness. The residue is then recrystallized from ethyl acetate and dried in a vacuum drying cabinet, thus obtaining 2.42 g (54.6% of theory) of 1-methylandrostadienedione, mp 164°–166° C. Another 0.45 g (10% of theory) of 1-methylandrostadienedione is obtained by purifying the crystallization mother liquor by column chromatography.

EXAMPLE 2

Under the conditions of Example 1, methenolone is converted to 1-methylandrostadienedione by using the strain *Mycobacterium rhodochrous* ATCC 4276.

EXAMPLE 3

Under the conditions of Example 1, but using a nutrient medium consisting of 3% glucose, 1% corn steep liquor, 0.2% NaNO$_3$, 0.1% KH$_2$PO$_4$, 0.2% K$_2$HPO$_4$, 0.05% MgSO$_4$. 7H$_2$O, 0.002% FeSO$_4$. 7H$_2$O and 0.5% KCl, methenolone is converted to 1-methylandrostadienedione by means of the strain *Fusarium solani* ATCC 12823.

I claim:

1. A process for the preparation of 1-methyl-1,4-androstadiene-3,17-dione, comprising fermenting 17$\beta$-hydroxy-1-methyl-5$\alpha$-androsten-1-en-3-one with a microorganism culture of *Rhodococcus rhodochrous* ATCC 14350 or *Rhodococcus rhodochrous* ATCC 4276, and isolating the thus-produced 1-methyl-1,4-androstadiene-3,17-dione.

2. A process according to claim 1, conducted in a nutrient medium wherein about 100–2000 mg of 17$\beta$-hydroxy-1-methyl-5$\alpha$-androsten-1-en-3-one is used per liter of nutrient medium.

3. A process according to claim 1, wherein the fermentation is conducted at a pH of 5–7.

4. A process according to claim 1, wherein the culture is incubated at 20°–40° C., and is aerated with about 0.5–5 liters of air per liter of culture broth.

* * * * *